US00PP27311P3

(12) United States Plant Patent
Klemm et al.

(10) Patent No.: US PP27,311 P3
(45) Date of Patent: Oct. 25, 2016

(54) ***PETUNIA* PLANT NAMED 'KLEPH14253'**

(50) Latin Name: *Petunia hybrida*
Varietal Denomination: KLEPH14253

(71) Applicant: Klemm+Sohn GmbH & Co. KG, Stuttgart (DE)

(72) Inventors: Nils Klemm, Stuttgart (DE); Antonella Capo, Latina (IT)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 91 days.

(21) Appl. No.: 14/545,077

(22) Filed: Mar. 23, 2015

(65) Prior Publication Data

US 2016/0286704 P1 Sep. 29, 2016

(51) Int. Cl.
*A01H 5/02* (2006.01)

(52) U.S. Cl.
USPC ..... Plt./356.23

(58) Field of Classification Search
USPC ..... Plt./356.1
See application file for complete search history.

*Primary Examiner* — Susan McCormick Ewoldt
*Assistant Examiner* — Karen Redden
(74) *Attorney, Agent, or Firm* — Bethany R. Roahrig; James M. Weatherly; Cochran Freund & Young, LLC

(57) ABSTRACT

A new *petunia* plant particularly distinguished by having salmon colored flowers with red veins and a mounding plant habit, is disclosed.

1 Drawing Sheet

Genus and species: *Petunia hybrida.*
Variety denomination: 'KLEPH14253'.

BACKGROUND OF THE NEW PLANT

The present invention comprises a new and distinct variety of *petunia*, botanically known as *Petunia hybrida*, and hereinafter referred to by the variety name 'KLEPH14253'. 'KLEPH14253' originated from a controlled-cross between the proprietary female *petunia* variety 'PH-2008-0219' (unpatented) and commercial male *petunia* variety Potunia Dark Red (patent status unknown).

In July 2010, two *petunia* parental lines, the female variety 'PH-2008-0219' and the male *petunia* variety Potunia Dark Red were crossed via a controlled cross in Latina, Italy and seeds were obtained. The seeds were sown and plants were grown for evaluation. A plant line was selected in April 2011 which had salmon colored flowers with red veins and was subsequently named 'KLEPH14253'. In April 2011, 'KLEPH14253' was first vegetatively propagated by terminal tip cuttings in Latina, Italy. 'KLEPH14253' was found to reproduce true to type in successive generations of asexual propagation via tissue culture and terminal tip cuttings.

SUMMARY

The following are the most outstanding and distinguishing characteristics of this new variety when grown under normal horticultural practices in Latina, Italy.

1. Salmon colored flowers with red veins; and
2. A mounding plant habit.

DESCRIPTION OF THE PHOTOGRAPH

This new *petunia* plant is illustrated by the accompanying photograph which shows the flowers and foliage of the plant.

The photograph is of a four-month-old plant grown outdoors in Stuttgart, Germany in July 2013. The colors shown are as true as can be reasonably obtained by conventional photographic procedures.

DESCRIPTION OF THE NEW VARIETY

The following detailed descriptions set forth the distinctive characteristics of 'KLEPH14253'. The data which define these characteristics were collected from asexual reproductions carried out in Latina, Italy. Data was collected on twelve-week-old plants grown in plastic greenhouse in Latina, Italy in February 2015. Color references are to The R.H.S. Colour Chart of The Royal Horticultural Society of London (R.H.S.), 5$^{th}$ edition (2007).

Classification:
- *Family.*—Solanaceae.
- *Species.*—*Petunia hybrida.*
- *Common name.*—*Petunia.*
- *Variety.*—'KLEPH14253'.

Parentage:
- *Female.*—Proprietary female *petunia* 'PH-2008-0219' (unpatented).
- *Male.*—Potunia Dark Red (patent status unknown).

Plant description:
- *Form.*—Medium compact.
- *Habit.*—Mounding.
- *Height (from top of soil).*—8.0 cm.
- *Width.*—16.0 cm.
- *Propagation.*—Terminal tip cuttings.
- *Time to produce a finished flowering plant.*—About 12 weeks in winter under short day conditions; 7 weeks in spring.
- *Time to initiate and develop roots.*—2 to 3 weeks.
- *Root description.*—Moderate density, moderate branching, white roots.

Stems:

*Average number* (*basal*).—About 12.

*Length of basal branches* (*from the base of the stem to the tip*).—About 9.0 cm.

*Internode length*.—0.6 cm to 2.0 cm.

*Diameter of branches* (*from midpoint*).—0.5 cm.

*Stem color*.—RHS 144C.

*Anthocyanin*.—Absent.

*Texture*.—Tomentose.

Leaves:

*Arrangement*.—Alternate.

*Length*.—About 3.0 cm.

*Width*.—1.5 cm.

*Shape*.—Elliptic/lanceolate.

*Apex*.—Acute.

*Base*.—Attenuate.

*Margin*.—Entire.

*Immature leaf color*.—Upper surface: RHS 137A. Lower surface: RHS 146B.

*Mature leaf color*.—Upper surface: Between RHS 137B and RHS 137C. Lower surface: RHS 146B.

*Texture* (*both surfaces*).—Tomentose.

*Venation pattern*.—Arcuate.

*Venation color*.—Upper surface: RHS 144B. Lower surface: RHS 146B.

*Petioles*.—Length: 0.3 cm. Diameter: 0.4 cm. Color: RHS 144B. Texture: Tomentose.

Flower buds:

*Shape*.—Irregular to oblong.

*Length*.—About 4.0 cm.

*Diameter*.—0.5 cm.

*Color at tight bud*.—RHS 186C.

*Texture*.—Slightly pubescent.

Inflorescence:

*Blooming habit* (*flowering season*).—Permanent flowering during the summertime.

*Inflorescence type*.—Cymose.

*Number of flowers per node*.—1.

*Lastingness of individual blooms on the plant*.—7 to 10 days.

*Fragrance*.—Absent.

*Flowers*.—Arrangement: Composed of 5 petals fused at the base. Shape: Funnel form. Diameter (flower face): 5.5 cm. Depth (total length of flower): 5.0 cm. Throat/Funnel: Length: 2.5 cm. Diameter (at opening): 1.0 cm. Texture (both inner and outer surfaces): Smooth, glabrous. Petals: Color of petals, immature flower: Upper surface: RHS 52B. Lower surface: RHS 51C. Color of petals, mature flower: Upper surface: RHS 50C. Lower surface: RHS 51C. Apex: Broadly mucronate. Base: Fused. Margin: Entire. Strength of waviness: Weak. Degree of lobation: Weak to medium. Calyx arrangement: Actinomorphic, composed of 5 sepals.

*Sepals*.—Color: Upper surface: Between RHS 137B and RHS 137C. Lower surface: RHS 144A. Length: 1.7 cm to 2.0 cm. Width: 0.2 cm. Shape: Linear. Apex: Narrowly acute. Base: Attenuate. Margin: Entire. Texture (both surfaces): Tomentose.

*Pedicels*.—Color: Between RHS 144A and RHS 144B. Length: 2.0 cm to 2.5 cm. Diameter: 0.2 cm. Texture: Tomentose.

Reproductive organs:

*Stamens*.—Quantity: 5. Shape: Needle like with elliptic head. Filament: Length: 1.2 cm to 1.5 cm. Diameter: 0.05 cm. Color: RHS 150D. Anther: Shape: Elliptic. Color: RHS 158B. Length: 0.2 cm. Diameter: 0.15 cm. Pollen: Color: RHS 158A. Amount: Moderate. Pistils: Quantity per flower: 1. Length: 2.0 cm. Stigma color: RHS 145A. Style color: Between RHS 145A and RHS 145B.

Fruit/seed set: None observed.

Disease/insect resistance: None observed.

COMPARISON WITH PARENTAL LINES AND KNOWN VARIETY

'KLEPH 14253' is a distinct variety of *petunia* and is distinguished from its parents as described in Table 1:

TABLE 1

Comparison with Parental Lines

| Trait | Variety 'KLEPH14253' | Female parent 'PH-2008-0219' | Male Parent Potunia Dark Red |
|---|---|---|---|
| Flower size | Bigger than 'PH-2008-0219' | Smaller than 'KLEPH14253' | |
| Flower color | Salmon with red veins | | Red |

'KLEPH14253' is most similar to the *petunia* plant named Bonnie Salmon Red Vein, also known as 'KLEPH13227' (U.S. Plant Pat. No. 26,354). Differences between the two varieties are described in Table 2:

TABLE 2

Comparison with Similar Variety

| Trait | Variety 'KLEPH14253' | Commercial line 'KLEPH13227 |
|---|---|---|
| Flower color | RHS 50C with red veins | RHS 62A with RHS 53A veins |

We claim:

1. A new and distinct variety of *petunia* plant named 'KLEPH14253' as illustrated and described herein.

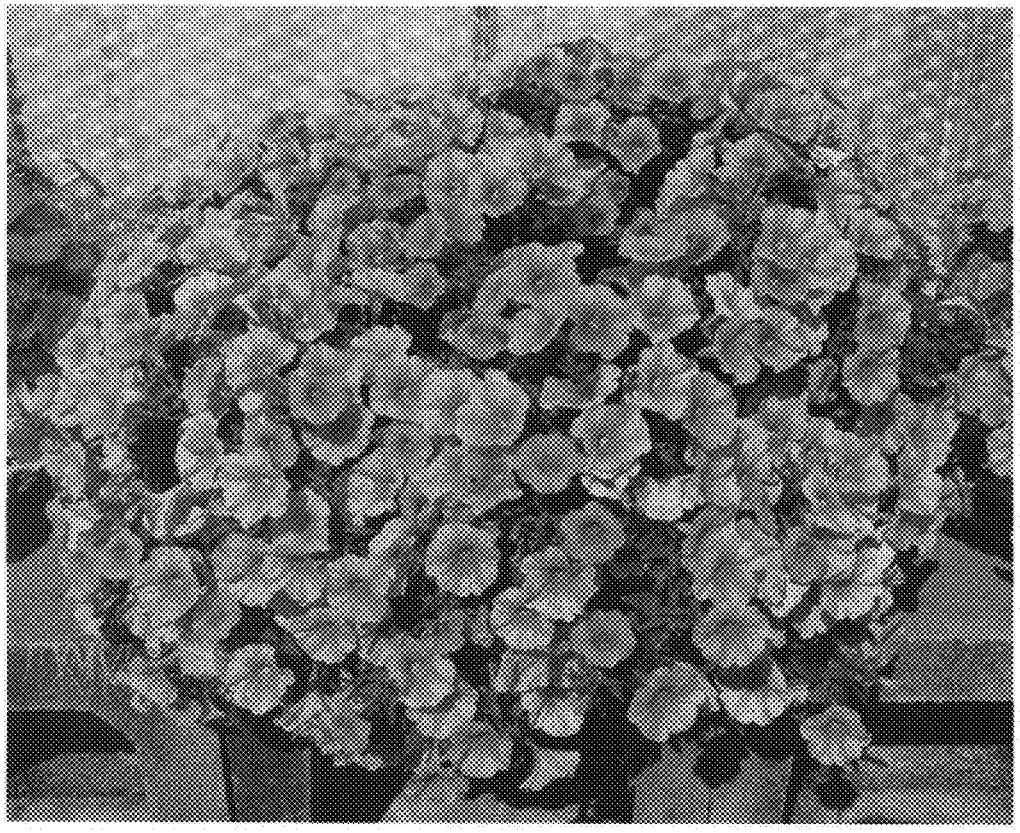

* * * * *